United States Patent
Pablos

(10) Patent No.: US 7,550,504 B2
(45) Date of Patent: Jun. 23, 2009

(54) METHOD FOR THE PRODUCTION ON METAL CARBOXYLATES AND THE METAL AMINOATE OR METAL HYDROXY ANALOGUE METHIONATE DERIVATIVES THEREOF, AND USE OF SAME AS GROWTH PROMOTERS IN ANIMAL FEED

(75) Inventor: Enrique Pablos, Madrid (ES)

(73) Assignee: Norel, S.A., Madrid (ES)

( * ) Notice: Subject to any disclaimer, the term of this patent is extended or adjusted under 35 U.S.C. 154(b) by 0 days.

(21) Appl. No.: 10/563,590

(22) PCT Filed: Jul. 9, 2004

(86) PCT No.: PCT/ES2004/070049

§ 371 (c)(1),
(2), (4) Date: Mar. 1, 2007

(87) PCT Pub. No.: WO2005/005365

PCT Pub. Date: Jan. 20, 2005

(65) Prior Publication Data

US 2007/0259954 A1    Nov. 8, 2007

(30) Foreign Application Priority Data

Jul. 11, 2003    (ES) ................................ 200301696

(51) Int. Cl.
*A61K 31/315*    (2006.01)
*A61K 31/30*    (2006.01)

(52) U.S. Cl. ........................ 514/494; 556/112; 556/118; 514/499

(58) Field of Classification Search ................. 556/112, 556/118; 514/494, 499
See application file for complete search history.

(56) References Cited

U.S. PATENT DOCUMENTS

| 5,504,055 | A | * | 4/1996 | Hsu ........................... 504/121 |
| 5,591,878 | A | | 1/1997 | Nelson et al. |
| 6,197,815 | B1 | | 3/2001 | Hsu |
| 6,607,761 | B2 | * | 8/2003 | Henry et al. ................... 426/74 |
| 6,716,814 | B2 | * | 4/2004 | Ericson et al. ................. 514/6 |

FOREIGN PATENT DOCUMENTS

| ES | 2 139 945 | 2/2000 |
| ES | 2 150 670 | 12/2000 |

OTHER PUBLICATIONS

Brinkhaus, F., et al. "Bioavailability of Zinc Propionate in Dogs" *The Journal of Nutrition*, (1998) vol. 128, pp. 2596S-2597S.
Menocal, J. A "Utilizacion de metionina-zinc y metionina-manganeso en dietas de pollo de engorda: parametros productivos e incidencia del sindrome ascito." *Tec Pecu Mex* (2004) pp. 113-119.
Torre, C, et al. "Utilizacion de aditivos en ruminates : vitaminas y aminoacidos protegidos" *XIV Curso de Especializacion Avances en nutricion y Alimentacion Animal* (2003) (2004) <URL:http://www.uco.es/servicios/nirs/fedna/capitulos/98_CAPIV.pdf>.

* cited by examiner

*Primary Examiner*—Porfirio Nazario Gonzalez
(74) *Attorney, Agent, or Firm*—Ladas & Parry LLP

(57) ABSTRACT

A process for preparing a feed supplement that promotes growth in animals by (i) preparing a dry metal carboxylate of formula M(RCOOH)2; (ii) preparing a metal aminoate; and (iii) mixing the dry metal carboxylate and the metal aminoate under conditions that form a complex including the metal carboxylate and the metal aminoate and water, then removing the water to form a dry metal complex of the metal carboxylate and the metal aminoate. When administered to an animal in its feed, a bioavailability of the divalent metal in the dry metal complex is different than the bioavailability of the divalent metal in either the dry metal carboxylate or the metal aminoate alone.

23 Claims, No Drawings

METHOD FOR THE PRODUCTION ON METAL CARBOXYLATES AND THE METAL AMINOATE OR METAL HYDROXY ANALOGUE METHIONATE DERIVATIVES THEREOF, AND USE OF SAME AS GROWTH PROMOTERS IN ANIMAL FEED

FIELD OF TECHNOLOGY

The present invention describes a method of production of metal carboxylates, concretely butyrates and formates of divalent metals, as well as their carboxylate-aminoate or carboxylate-methioninate hydroxy analog derivatives of divalent metals, for use as trace metal supplement in animal feed.

BACKGROUND OF THE INVENTION

There are at present two subjects of vital importance in the legal framework of the animal production sector: the use of antibiotics that are growth promoters and the emission of residues to the environment, of the trace elements necessary both for promoting said growth and incorporated in feed.

Regarding growth-promoter antibiotics, these display great efficacy for improving production yields and preventing certain diseases, so that for more than 50 years they have made it possible to reduce production costs considerably. However, owing to the controversy concerning the possible development of resistance in certain strains of bacteria and its consequences for public health, in March 2002 the Committee of the European Union proposed a ban on these additives, which will be applied starting from 2005. Considerable repercussions are to be expected in the animal production sector, owing to the large increase in the costs of production.

In the case of trace elements, the considerable genetic improvement and physical development of production animals have led to an increase in demand for these nutrients to satisfy the requirements and ensure optimum development. In this sense, however, waste disposal is increasingly being regulated by legislation and the maximum permitted levels for inclusion in feed are steadily decreasing. Therefore recourse is being had increasingly to new sources of minerals (organic sources of minerals) with greater bioavailability and, accordingly, less likely to be eliminated in the feces. It should be pointed out that some inorganic sources of minerals, such as copper sulfate and zinc oxide, when administered at high doses (250 ppm and 1500-3000 ppm respectively) produce a considerable growth-promoter effect, mainly through their bactericidal action in the intestine, but said doses are far higher than those laid down by the environmental legislation (175 and 250 ppm for copper and zinc, respectively), therefore we must also do without their benefits.

That is why in recent years the animal feed additives industry has devoted considerable effort to the development of new substances to replace growth-promoting antibiotics without posing a health risk, and to the search for organic sources of minerals that provide the levels required for optimum growth of the animal and greatly reduce the discharge of residues into the environment.

Organic acids have proved very effective as intestinal sanitizing agents and improvers of production parameters in livestock and they therefore represent one of the most suitable alternatives to growth-promoting antibiotics. Among them, formic acid and butyric acid can be regarded as the most effective in monogastric animals owing to their recognized bactericidal effect and growth stimulation of the intestinal villi, which improve intestinal integrity and increase the absorption of nutrients. Supplements of iron (Fe) in the diet of livestock, by means of formate (WO 99/62355), or supplements of chromium ($Cr^{+6}$) or manganese ($Mn^{+7}$), by means of propionates (WO 98/33398), are known in this context.

The organic sources of minerals available as supplements for animal nutrition comprise:
Metal chelates with amino acids: molar ratio from 1:1 to 1:3.
Metal/amino acid complexes: formed by covalent bonding of an (unspecified) amino acid and a metal.
Complexes of specific amino acids with a metal: constituted of a specific amino acid and a metal.
Proteinates: resulting from the chelation of a hydrolyzed protein with a metal.
Polysaccharide/metal complexes.
Metal carboxylates: salts of various carboxylic acids with divalent metals. Used for the most part as organic mineral supplements, with greater bioavailability than the inorganic sources.

Against this background, one of the objects of the present invention relates to the production of combined molecules of organic acids of recognized efficacy in animal production, concretely formic and butyric acids, and inorganic salts of zinc and copper. This combination displays a synergistic effect which boosts the effectiveness of both substances in improving the production parameters and increases the bioavailability of the metals, permitting the use of copper and zinc as promoter substances, but keeping their level of inclusion in the feed within the established legal limits.

Another object of the present invention is the production of derivatives of the aforementioned metal carboxylates which are carboxylate-aminoates of divalent metals or carboxylate-methioninate hydroxy analogs of divalent metals. This combination displays an even greater synergistic effect which boosts the effectiveness of these substances in improving the production parameters and increases the bioavailability of the metals, further facilitating the use of divalent metals as promoters, but keeping their level of inclusion in the feed within the established legal limits.

Another object of the present invention is to develop a method of production, both of metal carboxylates and of their metal carboxylate-aminoate or carboxylate-methioninate hydroxy analog derivatives, as an alternative to the conventional methods of synthesis in an aqueous medium that require the separation of the precipitated product from the solution and drying of said product.

A further object of the present invention is the use of the products obtained (metal carboxylates and their metal carboxylate-aminoate or metal carboxylate-methioninate hydroxy analog derivatives) as additives in the feed of monogastric production animals, with the aim of improving their productivity.

An advantage of the process described, relative to the conventional method in aqueous solution, is that it reduces the number of stages in the production process considerably, since operations such as product precipitation or filtration are avoided. Another advantage of this invention is that it provides a process for the production of carboxylates of divalent metals that is easy to implement on a large scale and at low cost since the process requires relatively low energy consumption. Furthermore, this method of production offers the additional advantage over the conventional method, that in some cases it increases the solubility with respect to some basic metal compounds. Yet another advantage of the invention is that an organic source of metal is obtained with a higher metal content.

Regarding its application, the compounds described in this specification have the advantage that their obvious growth-promoting effect in monogastric animals improves the production parameters, increasing the bioavailability of the metals and therefore reducing their emission to the environment.

DETAILED DESCRIPTION OF THE INVENTION

The present invention describes a method for the production of carboxylates ($C_1$, $C_4$) of divalent metals that correspond to the formula $M(RCOO)_2$, where M is the zinc ($Zn^{2+}$) or copper ($Cu^{2+}$) divalent metal cation and R corresponds to a proton for the formates and to the $CH_3(CH_2)_2$ group for the butyrates, and of their metal carboxylate-aminoate or metal carboxylate-methioninate hydroxy analog derivatives. The source of metal cation, M, in the case of the carboxylates and the methioninate hydroxy analogs is a basic compound of the metal such as oxide or hydroxide, concretely zinc(II) oxide and copper(II) hydroxide, and in the case of the aminoates the source of cation used is metal salts, such as zinc sulfate and copper sulfate and in the derivatives, in the carboxylate-aminoate derivatives a combination of the aforementioned sources of metal is used.

The carboxylates of divalent metal are prepared starting from the carboxylic acid by addition of the dry basic salt of the divalent metal, oxide of $Zn^{2+}$ or hydroxide of $Cu^{2+}$, without needing to add any kind of solvent. This is an advantage since the basic salts of the metals used in the present invention are sparingly soluble in water. The reactants are stirred together, giving rise to an exothermic reaction which produces water and the carboxylate of Zn(II) or Cu(II). The reaction mixture is stirred further in order to eliminate the water formed, so that the formate or butyrate is obtained dry and water-free.

Formation of the metal carboxylate-aminoates begins with a stage of preparation of the metal aminoate. Said compound is prepared from the amino acid and the metal compound; water is added to the amino acid, and between 0.1% and 0.3% of soda is added as neutralizing agent if required. The water is virtually eliminated by a vacuum drying process. The reaction mixture is kept stirred with the water at 90-98° C. for 20 min or longer, depending on the actual type of aminoate to be obtained, with the aim of obtaining the desired aminoate. Next the metal aminoate obtained is mixed with the metal carboxylate, subjecting the product to a process at temperature of 90-98° C. or to a vacuum process at lower temperature, depending on the product, to obtain the corresponding final product, adding absorbent if required.

The carboxylate-methioninate hydroxy analogs of divalent metal are prepared from the mixture of carboxylic acid and methionine hydroxy analog and addition of basic compound of divalent metal, without the need to add any type of solvent. The acid mixture is added slowly, stirring continuously, resulting in an exothermic reaction that produces water and a mixture of carboxylate-methioninate hydroxy analog of divalent metal. The reaction mixture is stirred further at a temperature of 90-98° C. or in vacuum at a lower temperature, for the purpose of removing practically all of the water formed, obtaining the dry carboxylate-methioninate hydroxy analog.

The butyric or formic acid and the basic compound of divalent metal are used in approximately stoichiometric quantities, with a molar ratio of carboxylic acid and metallic base of approximately 2:1, it being possible to work with an excess of 3-6 wt. %, both of the metal compound and of the carboxylic acid.

The amino acid and the metal compound are used in 1:1 molar ratio, working with excess of metal (1-3 wt. %).

The methionine hydroxy analog and the metal compound are used in 2:1 molar ratio, working with excess of metal (1-3 wt. %).

The formic acid used in the invention contains 15% water. The butyric acid contains 0.016% water. The methionine hydroxy analog contains 11.20% water. Glycine and methionine can be regarded as anhydrous reactants.

The commercially available metallic bases that are used do not contain water of crystallization, but the sulfates do. It is preferable to use these bases in the form of relatively small particles (particle size below 6.5 mm) to facilitate contact between the reactants and subsequent reaction.

Butyric acid melts at −7.9° C. and boils at 163.5° C. at 1 atm. Butyric acid forms an azeotrope with water which boils at 99.4° C. and contains 18.4% of butyric acid. As a result of formation of the azeotrope and the relatively low boiling point of the mixture, some of the butyric acid is lost with the water at the reaction temperature, and is recovered in the process by means of condensation and combination of soluble sodium salts or calcium salts that can be precipitated. Formic acid melts at 8.4° C. and boils at 100.5° C. at 1 atm. Formic acid forms an azeotrope with water which boils at 107.1° C. and contains 77.5% of formic acid. As a result of formation of the azeotrope and the relatively low boiling point of the mixture, some of the formic acid is lost with the water at the reaction temperature, and is recovered in the process by means of condensation and combination of soluble sodium salts or calcium salts that can be precipitated.

Both butyric acid and formic acid are used in liquid form.

Any reactor or equipment can be used for carrying out the reaction. In the case of small-scale reactions in the laboratory, a beaker was used as the reactor and a rod as the stirrer. For large-scale preparation, it is preferable to use a mixer equipped with mass stirrers and a lump-disintegrating intensifier turbine. After stirring, the reaction is completed in minutes but it is best to leave it to cool and dry for approximately one hour.

Reaction takes place exothermically according to the following equations:

Reaction of the metal salts:

$$Zn(II) \text{ butyrate: } ZnO+2CH_3(CH_2)_2COOH \rightarrow Zn(CH_3(CH_2)_2COO)_2+H_2O \qquad 1)$$

$$Cu(II) \text{ butyrate: } Cu(OH)_2+2CH_3(CH_2)_2COOH \rightarrow Cu(CH_3(CH_2)_2COO)_2+2H_2O \qquad 2)$$

$$Zn(II) \text{ formate: } ZnO+2HCOOH \rightarrow Zn(HCOO)_2+H_2O \qquad 3)$$

$$Cu(II) \text{ formate: } Cu(OH)_2+2HCOOH \rightarrow Cu(HCOO)_2+2H_2O \qquad 4)$$

$$\text{Metal methioninate hydroxy analog: } 2HMA+ZnO=Zn(MA)_2+H_2O \qquad 5)$$

$$\text{Metal methioninate hydroxy analog: } 2HMA+Cu(OH)_2=Cu(MA)_2+H_2O \qquad 6)$$

Reaction of formation of chelates:

$$\text{Metal amino acid: Amino acid (e.g. glycine)+Source of metal=MAm} \qquad 1)$$

When the carboxylic acid and the basic metal compound react there is evolution of water and heat. The water and a proportion of the acid are eliminated continuously from the reaction medium by the heat of reaction, continuous stirring of the product and/or a vacuum cleaning system.

In the preparation of zinc formate, the heat of reaction is sufficient to evaporate the water that forms. In the preparation of zinc butyrate, copper butyrate and copper formate it is necessary to assist this by supplying additional heat.

The result is a dry product in the form of powder in the case of the butyrates. Both zinc formate and copper formate are obtained as large particles which require grinding.

The divalent metal carboxylates prepared by this process are obtained at yields of around 80%, although values of 90% may be reached. Losses are recovered by means of a gas recovery system with condensers and combination with soluble sodium salts or calcium salts that can be precipitated. The products are obtained in the form of dry powder but may form lumps owing to the presence of small amounts of unreacted acid. In these cases it is preferable to employ grinding to obtain a product that could be used directly as a feed supplement. This production process avoids post-reaction treatments such as, among others: concentration, crystallization, separation by filtration, decanting or centrifugation and freeze-drying, which requires the conventional aqueous method, saving energy and costs.

In the case of the carboxylate-aminoates, the solution thickens in the preceding stage of formation of the aminoate from the amino acid and the salt in aqueous medium. The compound obtained is mixed with the metal carboxylate described previously and the water is removed by means of the vacuum cleaning system with addition of silica if appropriate.

In the case of formation of the carboxylate-methioninate hydroxy analog, when the basic metal compound is added to the mixture of carboxylic acid and hydroxy analog of methionine, water and heat are generated. The water is eliminated continuously from the reaction medium by the heat of reaction and continuous stirring of the product and/or vacuum cleaning system.

EXAMPLES OF MANUFACTURE OF METAL CARBOXYLATES

Processes at the Laboratory Scale

Example 1

Zinc butyrate

Zinc butyrate was prepared by adding 20.25 g of ZnO to 44 g of butyric acid, in a beaker (stoichiometric proportions ZnO:butyric acid 1:2). The reactants were mixed rapidly by stirring with a glass rod, allowing the vapors formed to escape from the beaker. The reaction reached a temperature of 55° C. After stirring for 5 minutes, the product is obtained as a moist white solid which is passed through a cooling screw or at room temperature which removes it to dry it more quickly and make it available for grinding to the granulometry required for marketing. A product with more than 90% of zinc butyrate was obtained.

Example 2

Copper butyrate

Copper butyrate was prepared by adding 26.5 g of $Cu(OH)_2$ to 44 g of butyric acid, in a beaker (proportions $Cu(OH)_2$:butyric acid 1.1:2). The reactants were mixed rapidly, stirring with a glass rod and allowing the vapors that form to escape from the beaker. The reaction reached a temperature of 65° C. After stirring for 5 minutes, the product is obtained in the form of a moist greenish-blue solid which is passed through a cooling screw or at room temperature which removes it to dry it more quickly and make it available for grinding to the granulometry required for marketing. A product with more than 90% of copper butyrate was obtained.

Example 3

Zinc formate

Zinc formate was prepared by adding 21.75 g of ZnO to 27 g of formic acid (85%), in a beaker (proportions ZnO:formic acid 1.1:2). The reactants were mixed rapidly, stirring with a glass rod and allowing the vapors that form to escape from the beaker. The highly exothermic reaction reached a temperature of 120° C. After stirring for 5 minutes, the product is obtained in the form of a moist white solid which is passed through a cooling screw or at room temperature which removes it to dry it more quickly and make it available for grinding to the granulometry required for marketing. A product with more than 85% of zinc formate was obtained. Final grinding of the product is required.

Example 4

Copper formate

Copper formate was prepared by adding 24.5 g of $Cu(OH)_2$ to 27 g of formic acid (85%), in a beaker (stoichiometric proportions $Cu(OH)_2$:formic acid 1:2). The reactants were mixed rapidly, stirring with a glass rod and allowing the vapors that form to escape from the beaker. The reaction reached a temperature of 65° C. After stirring for 5 minutes, the product is obtained in the form of a fairly moist blue solid which is passed through a cooling screw or at room temperature which removes it to dry it more quickly and make it available for grinding to the granulometry required for marketing. A product with more than 85% of copper formate was obtained. Final grinding of the product is required.

When working in the laboratory it is preferable to separate the water produced in the reaction in the form of steam but in large-scale operation it can be aspirated from the exothermic reaction mixture under reduced pressure (vacuum). It is preferable to use a well insulated mixer in order to retain the heat that is released by the reaction and evaporate the water from the product.

Processes on an Industrial Scale

Operation on an industrial scale employs a first reactor-mixer (stirred tank reactor, STR) with a double-saw flat-disk agitator of the Cowles type from 1500 to 3000 rpm, connected via a discharge outlet with a sluice gate or gate valve to reactor plant (MHT 1200). This discharge outlet comprises a hermetic closure system with pneumatic operation to permit fast discharge from the reactor. The second reactor comprises blades of the plow type, mass agitators from 200 to 400 rpm and two intensifier/delumping turbines from 1500 to 3000 rpm. The reactor also comprises a double jacket with hot oil or preferably steam, at a temperature from 80 to 130° C. (preferably between 90 and 110° C.). Apart from the movement of the agitator blades, the equipment comprises vacuum by means of a cyclone-aspirator in line, passing said aspirated material firstly through a bag filter which separates the solids from the vapors produced by the reaction and, secondly, the vapor from which the solids have already been removed is directed into a condensing heat exchanger, recovering the water of reaction with some acid (1-2%) for later treatment.

Lastly, the remaining vapor passes through a gas scrubber, with dissolution of NaOH at 25% for neutralizing the acidic vapors produced. A negative-pressure sealed enclosure is used, collecting all the vapors to be treated, avoiding emission of harmful vapors to the exterior (bad odors). In conclusion, both the water of reaction and any vapor remain perfectly controlled and clean, for use in this process itself or in other processes. Separate machines are used, one for the products containing zinc and another for the copper products.

From the stainless steel storage tanks (INOX AISI-304L) which receive the carboxylic acid, the required amount of acid is injected into the first reactor with a magnetic proportioner. At the same time as the carboxylic acid, the basic compound of divalent metal is added by means of a proportioner with load cells, keeping the mixture stirred for a time of from 2 to 30 seconds. After this time, the discharge outlet with sluice valve that separates the two reactors is opened and the reaction mixture is allowed to descend to the second reactor, where stirring continues for between 1 and 5 minutes with the plow-type blades, operating at between 200 and 600 rpm and the intensifier turbines between 1500 and 3000 rpm.

On completion of reaction, the equipment is sealed and the vacuum is switched on, which will draw off, in the form of steam, the water molecules produced in the same reaction together with some of the acid (between 1 and 2%). To complete this extraction more immediately, the intensifier turbines are operated at between 1500 and 3000 rpm and will break up any lumps and ensure faster release of moisture from the particles, assisted by the heat of reaction and the heat of the double jacket with hot oil or preferably steam between 80 and 130° C. Total process time is between 20 and 70 minutes.

Example 5

Copper Butyrate, on an Industrial Scale 200 kg of copper butyrate was prepared in the equipment described previously. Firstly the first reactor was charged with 140 kg of butyric acid and 85 kg of Cu(OH)$_2$, stirring with the double-saw flat-disk agitator at 2000 rpm for 30 s. After this time, the discharge outlet with sluice valve was opened, allowing the product to descend to the second reactor, where it was stirred for 2 minutes with the plow-type blades at 400 rpm and the intensifier turbines at 2000 rpm. Then the discharge outlet was closed, the vacuum was switched on to draw off the steam produced and the intensifier turbine was switched on at 2000 rpm to break up the lumps that had formed and assist in removal of the water. The reaction temperature is 65° C., so it was necessary to help with the double jacket of hot oil or preferably steam, at 120° C. to obtain a dry greenish-blue product in powder form. The total losses in the reaction are 11%, with a loss of butyric acid of 1.3% and with a product purity of more than 90%. Total process time was approximately 50 minutes.

Examples Of Manufacture Of Metal Carboxylate-aminoates

For preparation of metal carboxylate-aminoates on an industrial scale, the method is changed as follows: The second reactor of the Lödige type is loaded with the basic metal compound by means of a proportioner with load cells or other metering system. From the stainless steel storage tanks (INOX AISI-403L) where the carboxylic acid is received, the required amount of acid is injected slowly into this second reactor of the Lödige type using a magnetic proportioner, while stirring with the plow-type blades operating between 200 and 600 rpm. After this time during which the acid is added, the intensifier turbines are switched on between 1500 and 3000 rpm.

While the metal carboxylate is in the second reactor, manufacture of the metal aminoate is carried out in the first reactor. Water at 90° C. and zinc sulfate or metal derivative depending on the compound are added, stirring until it dissolves. Then, in the case of the aminoate, the amino acid is added and between 0.1% and 0.3% of soda is added as neutralizing agent if required, stirring until chelation is completed. On completion of chelation, the discharge outlet with sluice valve separating the two reactors is opened and the reaction mixture is allowed to descend to the second reactor.

Once all of the aminoate has been poured onto the carboxylate, the equipment is sealed and the vacuum is switched on, and will be maintained until the final product has been discharged. The vacuum system will draw off, in the form of steam, the water molecules produced in the same reaction with a proportion of the acid (between 1 and 2%), and the water arising from the chelation process. To complete this extraction more immediately, the intensifier turbines are operated at between 1500 and 3000 rpm and will break up any lumps and ensure faster release of moisture from the particles, assisted by the heat of the reaction and the heat of the double jacket with hot oil or preferably steam between 80 and 130° C. Absorbent is added if required. Total process time is between 20 and 70 minutes. The dry product obtained is submitted to an additional grinding operation.

The order can be changed without any significant effect on product quality.

Example 6

Zinc formate-aminoate(glycinate) (50%-50%), on an Industrial Scale 800 kg of zinc formate was prepared using the equipment described previously. Firstly the reactor of the Lödige type was charged with 446 kg of ZnO and 554 kg of formic acid (85%) was added slowly, stirring with the plow-type blades at 400 rpm. Then the mouth of the equipment was closed, the vacuum was switched on to draw off the water vapor produced and the intensifier turbine was switched on at 2000 rpm to break up the lumps that had formed and promote the removal of water. The reaction temperature is 110-120° C. After stirring for 5 minutes, the product is obtained as a moist white solid.

While the carboxylate is being produced in the reactor of the Lödige type, 131.3 kg of water and 686 kg of metal salt (zinc sulfate heptahydrate) are added to the first stirred tank reactor, then 180.1 kg of amino acid and 2.6 of soda are added, maintaining the jacket of the vessel at 90° C. and stirring continuously.

After 20 minutes, 70 kg of absorbent is added and the aminoate is poured onto the carboxylate, followed by the drying process. Finally grinding is carried out to obtain the granulometry required for marketing. The final product obtained contains 30% Zn, of which 30% is from the aminoate and 70% from the carboxylate.

Example 7

Zinc formate-aminoate(methioninate) (50%-50%), on an Industrial Scale 800 kg of zinc formate was prepared using the equipment described previously. Firstly, the first reactor was charged with 446.0 kg of ZnO and 554.0 kg of formic acid (85%), stirring with the double-saw flat-disk agitator at 2000 rpm for 30 seconds. After this time, the discharge outlet with sluice valve was opened, allowing the product to descend to the second reactor, where it was stirred for 2 minutes with the plow-type blades at 400 rpm and the intensifier turbines at 2000 rpm. Then the discharge outlet was closed, the vacuum was switched on to draw off the water vapor produced and the intensifier turbine was started up at 2000 rpm to break up the lumps that had formed and promote removal of the water. The reaction temperature is 110-120° C. After stirring for 5 minutes, the product is obtained as a moist white solid.

After transferring the carboxylate from the stirred tank reactor to the second reactor of the Lödige type, and in parallel, 232.1 kg of water and 510.4 kg of metal salt (zinc sulfate heptahydrate) are added to the first reactor, then 255.3 kg of amino acid and 2.3 of soda are added, maintaining the jacket of the vessel at 90° C. and stirring continuously.

After 20 minutes, 70 kg of absorbent is added and the aminoate is poured onto the carboxylate, and the drying process is carried out. Finally grinding is carried out to obtain the granulometry required for marketing. The final product obtained contains 28% Zn, of which 25% is from the aminoate and 75% from the carboxylate.

Example 8

Copper formate-aminoate(methioninate) (50%-50%), on an Industrial Scale 800 kg of copper formate was prepared using the equipment described previously. Firstly, the first reactor was charged with 486.0 kg of $Cu(OH)_2$ and 524.0 kg of formic acid (85%), stirring with the double-saw flat-disk agitator at 2000 rpm for 30 s. After this time the discharge outlet with sluice valve was opened, allowing the product to descend to the second reactor, where it was stirred for 2 minutes with the plow-type blades at 400 rpm and the intensifier turbines at 2000 rpm. Next, the discharge outlet was closed, the vacuum was switched on to draw off the water vapor produced and the intensifier turbine was switched on at 2000 rpm to break up the lumps that had formed and promote removal of the water. The reaction temperature is 110-120° C. After stirring for 5 minutes, the product is obtained as a moist blue solid.

After transferring the carboxylate from the stirred tank reactor to the second reactor of the Lödige type, and in parallel, 131.3 kg of water and 542.0 kg of metal salt (copper sulfate pentahydrate) are added to the first reactor, then 324.1 kg of amino acid and 2.6 of soda are added, maintaining the jacket of the vessel at 90° C. and stirring continuously.

After 20 minutes, 70 kg of absorbent is added and the aminoate is poured onto the carboxylate, and the drying process is carried out. Finally grinding is carried out to obtain the granulometry required for marketing. The final product obtained contains 27% Cu, of which 25% is from the aminoate and 75% from the carboxylate.

Production of Carboxylate-methioninate Hydroxy Analogs

For the case of carboxylate-methioninate hydroxy analog, the procedure is described below:

The basic metal compound is added to the second reactor of the Lödige type by means of a proportioner with load cells, and a quantity of product that has already reacted. From the stainless steel storage tanks (INOX AISI-304L), where the mixture of carboxylic acid and methioninate hydroxy analog is received, the required amount of acid mixture is injected slowly into this second reactor of the Lödige type using a magnetic proportioner, stirring with the plow-type blades operating at between 200 and 600 rpm. After this time for addition of the acid, the intensifier turbines are switched on at between 1500 and 3000 rpm to break up any lumps and ensure faster release of moisture from the particles, assisted by the heat of the reaction and the heat of the double jacket with hot oil or preferably steam between 80 and 130° C. Total process time is between 20 and 70 minutes.

Example 9

Zinc formate-methioninate hydroxy analog (HMA) (70%-30%), on an Industrial Scale The industrial-scale example of zinc formate-methioninate hydroxy analog is described below. 296.70 kg of ZnO is added to the second reactor of the Lödige type by means of a proportioner with load cells or some other metering system. From the stainless steel storage tanks (INOX AISI-304L), 166.20 kg of formic acid (85%) and 564.10 kg of HMA (88.80%) are injected into the first reactor of the STR type, the acids are mixed together, at room temperature and at atmospheric pressure, until uniform dissolution is achieved. At the end of stirring, the discharge outlet with diaphragm-type valve separating the two reactors is opened and allowed to transfer slowly onto the zinc oxide. While the mixture of acids is being added, stirring with the plow-type blades continues at 400 rpm and the vacuum that will draw off, throughout the manufacturing operation, the water vapor that is produced in the same reaction and a proportion of the mixture of acids (between 1 and 2%). Furthermore, to complete this extraction more immediately, the intensifier turbines are operated at between 1500 and 3000 rpm to break up any lumps and ensure faster release of moisture from the particles, assisted by the heat of the reaction 60-70° C. and the heat of the double jacket, a temperature of 90° C. is maintained, which also promotes evaporation of the water. Total process time is between 20 and 70 minutes.

Finally, grinding is carried out to obtain the granulometry required for marketing. The final product obtained contains 27% of Zn, of which 50% is from the methioninate hydroxy analog and 50% from the carboxylate.

Comparative Tests of Efficacy

Tests of Efficacy of Metal Carboxylates

Example 10

Test Of Efficacy In Broilers: (Chicken 7 Weeks Old, Ready for Consumption)

Objectives:

To determine the effectiveness of copper formate and copper butyrate on the production parameters of broilers.

Materials and Methods

Animals and Housing:

1600 one-day old broilers of the Ross strain were used (without differentiation of sexes), housed in 40 pens of 4 m².

Experimental Treatments

Five experimental treatments were used, comprising the same basic diet supplemented with different sources of copper:

T-0: Base diet+0.0056% copper sulfate (20 ppm of copper)
T-1: Base diet+0.0055% copper formate (20 ppm of copper)
T-2: Base diet+0.0073% copper butyrate (20 ppm of copper)
T-3: Base diet+0.0417% copper sulfate (150 ppm of copper)

The dose of copper added was calculated taking into account the natural copper content of the ingredients of the feed (about 15 ppm) and the maximum permitted dose in the finished feed (35 ppm of copper) in the case of treatments T-0 to T-2, and the dose with promoter effect (170 ppm of copper) in the case of treatment T-3. By adding 20 ppm of copper in the form of copper formate or butyrate to the feed, we aimed to obtain the same promoter effect as with the dose of 170 ppm of copper added as copper sulfate, but complying with the established legal levels.

The composition of the diets and their analysis are presented in Tables 1, 2 and 3.

The experimental model was a design of random blocks, with 8 replications per treatment. Each replication comprised a batch of 40 animals.

Controls

Control of production parameters was effected at 21 and 42 days of age, recording the live weight and the consumption of feed per batch.

On day 42 of the experiment, 2 animals were selected at random from each batch and were placed in cages in pairs according to their origin with respect to batch and previous treatment. During the next 4 days, an investigation of the bioavailability of the copper was carried out. After fasting for 20 hours, the live weight per cage was recorded and the experimental feeds were supplied for 2 days, recording the consumption of feed. After fasting again for 20 hours, the birds were weighed again per cage. All of the excrement was collected per cage for the entire period when weight records were kept. After weighing and homogenizing all of the excrement, a representative sample was taken from each cage for performing the analysis for copper. The copper excreted was calculated as a percentage of the copper ingested.

Statistical Analysis:

An analysis of variance was carried out using the GLM (generalized linear model) procedure of the SAS® statistical software (SAS Institute, 1996) applying the random block model.

Results

The results for the production parameters are shown in Table 4. Treatments T-1 to T-3 produced better production parameters relative to the control, in all the periods. The consumption of feed was slightly less for the birds fed with copper butyrate, which produced an improvement in the conversion index, but this was not significant. Thus, copper sulfate administered at a dose of 150 ppm produced growth-promoting effects relative to the control, as is already known. The administration of lower doses of copper in the form of copper formate and butyrate (20 ppm) produced the same promoter effect as the 150 ppm dose in the form of copper sulfate.

The results for copper bioavailability are shown in Table 5. The highest bioavailability was observed in treatments with copper formate and butyrate, demonstrating greater absorption of this mineral form in the intestine.

The supplementation of diets for broilers with copper in the form of butyric and formic salts at the doses laid down by the legislation produces an improvement in the production parameters, which can be regarded as a growth-promoter effect. Moreover, said sources of copper display greater bioavailability, so there is less emission of residues to the environment.

TABLE 1

Composition of the experimental diets:

|  | 0-21 d | 21-42 d |
|---|---|---|
| Ingredients |  |  |
| Wheat | 38.000 | 48.000 |
| Maize | 22.579 | 16.050 |
| Soya, 47% | 28.703 | 26.560 |
| Soya, extruded | 2.877 | 3.831 |
| Lard | 2.780 | 2.540 |
| DL-methionine | 0.259 | 0.238 |
| L-lysine HCl | 0.177 | 0.104 |
| Calcium carbonate | 1.269 | 0.697 |
| Dicalcium phosphate | 1.486 | 1.259 |
| Salt | 0.446 | 0.312 |
| Minerals and vitamins[1] | 0.400 | 0.400 |
| Choline chloride, 50% | 0.023 | 0.012 |
| Potato protein | 1.000 |  |
| Analysis |  |  |
| Gross protein, % | 21.02 | 20.7 |
| Gross fat, % | 9.21 | 1.14 |
| Gross fiber, % | 4.85 | 1.02 |
| Moisture, % | 8.61 | 0.90 |

[1]Copper-free vitamin-mineral supplement.

TABLE 2

Addition of sources of copper (%)

| Ingredients | T-0 | T-1 | T-2 | T-3 |
|---|---|---|---|---|
| Copper sulfate | 0.0056 |  |  | 0.0417 |
| Copper formate |  | 0.0055 |  |  |
| Copper butyrate |  |  | 0.0073 |  |

TABLE 3

Analysis of copper content (ppm)

| Treatment | 0-21 d | 21-42 d |
|---|---|---|
| T-0 | 33.25 | 35.20 |
| T-1 | 32.60 | 31.9 |
| T-2 | 34.56 | 34.8 |
| T-3 | 172.5 | 167.2 |

TABLE 4

Production parameters

| Treatment | 0-21 days | | | | 21-42 days | | | | 0-42 days | | |
|---|---|---|---|---|---|---|---|---|---|---|---|
|  | LW 21 d (g) | MDG (g) | MDC (g/d) | IC | LW 42 d (g) | MDG (g) | MDC (g/d) | IC | MDG (g) | MDC (g/d) | IC |
| T-0 | 716[a] | 34.2[a] | 48.9 | 1.43[a] | 2172[a] | 69.2[a] | 149.3 | 2.16[a] | 50.6[a] | 98.2 | 1.94[a] |
| T-1 | 755[b] | 36.1[b] | 49.6 | 1.37[b] | 2360[b] | 76.3[b] | 152.5 | 2.00[b] | 55.1[b] | 99.3 | 1.80[b] |

TABLE 4-continued

Production parameters

| | 0-21 days | | | | 21-42 days | | | | 0-42 days | | |
|---|---|---|---|---|---|---|---|---|---|---|---|
| Treatment | LW 21 d (g) | MDG (g) | MDC (g/d) | IC | LW 42 d (g) | MDG (g) | MDC (g/d) | IC | MDG (g) | MDC (g/d) | IC |
| T-2 | 763[b] | 36.2[b] | 48.9 | 1.35[b][a] | 2358[b] | 75.9[b] | 147.2 | 1.94[b] | 55.1[b] | 97.2 | 1.76[b] |
| T-3 | 756[b] | 35.9[b] | 49.7 | 1.38[b] | 2362[b] | 76.7[b] | 154.2 | 2.01[b] | 55.2[b] | 99.5 | 1.80[b] |
| S.E. | 11.4 | 0.5 | 0.76 | 0.014 | 35.02 | 1.32 | 2.52 | 0.036 | 1.23 | 1.27 | 0.031 |
| Sig. | * | * | N.S | * | * | * | N.S | * | * | N.S | * |

[a],[b]: Values in the same column with different superscript differ significantly (P < 0.05)
LW: Live weight; MDG: mean daily gain; MDC: mean daily consumption; IC: index of conversion S.E: Standard error;
Sig.: significance

TABLE 5

Copper balance from 43 to 46 days of age:

| Treatment | Consumption of feed (g) | Copper ingested (mg) | Copper excreted (mg) | Bioavail-ability % |
|---|---|---|---|---|
| T-0 | 206 | 7.3[a] | 4.08[a] | 43.73[a] |
| T-1 | 222 | 7.1[a] | 3.12[a] | 55.94[b] |
| T-2 | 210 | 7.3[a] | 2.99[a] | 59.09[b] |
| T-3 | 206 | 652.4[b] | 397.3[b] | 39.11[3] |
| S.E. | 3.6 | 3.2 | 2.6 | 1.01 |
| Sig. | N.S. | * | * | * |

[a],[b]Values in the same column with different superscript differ significantly (P < 0.05)

Example 11

Test of Efficacy in Piglets

Objectives:

To determine the effectiveness of zinc formate and zinc butyrate on the production parameters of recently weaned piglets.

Materials and Methods

Animals and Housing:

300 piglets were used (cross of Large White and Landrace), 50% males and 50% females, weaned at 21 days of age and housed in 30 pens with 10 animals in each (5 males and 5 females).

Experimental Treatments

Five experimental treatments were used, comprising the same basic diet, to which different sources of zinc are added:
T-0: Base diet+0.0275% zinc oxide (220 ppm of zinc)
T-1: Base diet+0.0560% zinc formate (220 ppm of zinc)
T-2: Base diet+0.0797% zinc butyrate (220 ppm of zinc)
T-3: Base diet+0.2463% zinc oxide (1970 ppm of zinc)

The zinc dose was calculated taking into account the zinc content of the ingredients of the feed and the maximum permitted dose (250 ppm of zinc in the finished feed) in the case of treatments T-0 to T-2, and the dose with promoter effect (2000 ppm) in the case of treatment T-3. By adding 220 ppm of zinc in the form of zinc formate or butyrate to the feed, we hoped to obtain the same promoter effect as with the dose of 1970 ppm of copper added as zinc oxide, but complying with the established legal levels.

The composition of the diets and their analysis are presented in Tables 6, 7 and 8. The experimental period was 21 days.

The experimental model was a design of random blocks, with 6 replications per treatment. Each replication comprised a batch of 10 animals.

Controls

Control of production parameters was effected at the end of the experiment, recording the live weight, the daily growth and the consumption of feed.

At the end of the experiment, one male and one female were selected at random from each batch to take a specimen of liver tissue and determine the zinc content.

Statistical Analysis:

An analysis of variance was carried out using the GLM (generalized linear model) procedure of the SAS® statistical software (SAS Institute, 1996) applying the random block model.

Results

The results for the production parameters are shown in Table 9. Treatments T-1 to T-3 produced better production parameters relative to the control, in all the periods. The consumption of feed was slightly less for the birds fed with zinc butyrate and formate, which produced an improvement in the conversion index, but this was not significant. Thus, zinc oxide administered at a dose of 1970 ppm produced growth-promoting effects relative to the control, as is already known. The administration of lower doses of zinc in the form of zinc formate and butyrate (220 ppm) produced the same promoter effect as the 1970 ppm dose.

The results for the liver zinc concentration are shown in Table 10. The highest concentration was observed in treatment with zinc oxide at a dose of 1970 ppm and the lowest in treatment with zinc oxide at a dose of 220 ppm. Determination of the ratio of zinc in the liver to zinc in the diet shows that the highest ratio occurs in animals fed with zinc formate and butyrate, indicating greater bioavailability of zinc when it forms formic and butyric salts.

When the diet of piglets is supplemented with zinc in the form of butyric and formic salts at the doses laid down by the legislation, there is an improvement in the production parameters, which can be regarded as a growth-promoter effect. Moreover, these sources of zinc display greater bioavailability, so that there is less emission of residues to the environment.

TABLE 6

Composition of the experimental diets:

|  | 21-42 d |
|---|---|
| Ingredients | |
| Maize | 30.0 |
| Wheat | 5.0 |
| Barley | 15.0 |
| Soya (full fat) | 14.0 |
| Fish meal | 9.9 |
| Soya flour (47%) | 2.0 |
| Soya oil | 1.9 |
| Delactosed whey | 3.1 |
| Sweet whey | 17.0 |
| L-lysine (78%) | 0.2 |
| L-threonine (99%) | 0.14 |
| Methionine-OH | 0.18 |
| Calcium carbonate | 0.34 |
| Dicalcium phosphate | 0.85 |
| Vitamin-mineral complex[1] | 0.3 |
| Analysis | |
| Gross protein, % | 21.02 |
| Gross fat, % | 7.20 |
| Gross fiber, % | 2.52 |
| Moisture, % | 8.40 |

[1] Zinc-free vitamin-mineral supplement.

TABLE 7

Addition of sources of zinc to the feed (%)

| Ingredients | T-0 | T-1 | T-2 | T-3 |
|---|---|---|---|---|
| Copper sulfate | 0.0275 | | | 0.2463 |
| Copper formate | | 0.0560 | | |
| Copper butyrate | | | 0.0797 | |

TABLE 8

Analysis of zinc content in the diets (ppm)

| Treatment | Zinc |
|---|---|
| T-0 | 241.2 |
| T-1 | 232.2 |
| T-2 | 252.3 |
| T-3 | 1963.2 |

TABLE 9

Production parameters from 21 to 42 days:

| | 21-28 days | | | | 21-42 days | | | |
|---|---|---|---|---|---|---|---|---|
| Treatment | LW 28 d (kg) | MDG (g) | MDC (g/d) | IC | LW 42 d (kg) | MDG (g) | MDC (g/d) | IC |
| T-0 | 8.41$^A$ | 244.5$^A$ | 321.7 | 1.32$^a$ | 13.11$^a$ | 475.3$^a$ | 795.3 | 1.67$^a$ |
| T-1 | 8.76$^{ab}$ | 268.6$^B$ | 312.3 | 1.16$^b$ | 14.30$^b$ | 512.6$^b$ | 752.3 | 1.47$^b$ |
| T-2 | 8.99$^B$ | 262.9$^{ab}$ | 286.3 | 1.09$^b$ | 14.15$^b$ | 509.6$^b$ | 741.3 | 1.45$^b$ |
| T-3 | 9.01$^B$ | 273.5$^B$ | 312.2 | 1.14$^b$ | 13.97$^{ab}$ | 511.3$^b$ | 763.2 | 1.49$^b$ |
| S.E. | 0.12 | 6.3 | 7.5 | 0.014 | 0.27 | 8.26 | 11.62 | 0.011 |
| Sig. | * | * | N.S | * | * | * | N.S | * |

$^{a,b}$: Values in the same column with different superscript differ significantly (P < 0.05)
LW: Live weight; MDG: mean daily gain; MDC: mean daily consumption; IC: index of conversion S.E: Standard error; Sig.: significance

TABLE 10

Zinc concentration in the liver (μg/g):

| Treatment | Liver zinc | Ratio Zn in liver/Zn in diet |
|---|---|---|
| T-0 | 47.63$^a$ | 19.5$^{ab}$ |
| T-1 | 59.21$^a$ | 25.5$^c$ |
| T-2 | 56.3$^a$ | 22.3$^{bc}$ |
| T-3 | 298.5$^b$ | 15.2$^a$ |
| S.E. | 2.6 | 0.47 |
| Sig. | * | * |

$^{a,b,c}$Values in the same column with different superscript differ significantly (P < 0.05)

Comparative Tests of Efficacy of Aminoate-Carboxylates

Example 12

Test in Broilers

Objectives:

To compare the effectiveness of the zinc aminoate (methioninate) products with zinc formate and with the product obtained by combining both compounds which will be called zinc methioninate-formate complex hereinafter, on the production parameters for broilers.

Materials and Methods

Animals and Housing:

192 one-day old broilers of the Ross strain were used (without differentiation of sexes), housed in 16 cages of 4 m².

Experimental Treatments

Four experimental treatments were used, comprising the same basic diet supplemented with different sources of zinc:

T-0: Base diet+50 ppm of zinc in the form of zinc sulfate
T-1: Base diet+50 ppm of zinc in the form of zinc formate
T-2: Base diet+50 ppm of zinc in the form of zinc methioninate
T-3: Base diet+50 ppm of zinc in the form of zinc methioninate-formate complex The dose of zinc was calculated taking into account the zinc content of the ingredients and the zinc requirements in the case of treatments T-0 to T-3. The composition of the diets and their analysis are presented in Tables 1 and 2.

Controls

Control of production parameters was effected at 21 and 42 days of age, recording the live weight and the consumption of feed per batch.

On day 42 of the experiment, 2 animals were selected at random from each batch and were placed in cages in pairs according to their origin with respect to batch and previous treatment. During the next 4 days, an investigation of zinc bioavailability was carried out. After fasting for 20 hours, the live weight per cage was recorded and the experimental feeds were supplied for 2 days, recording the consumption of feed. After fasting again for 20 hours, the birds were weighed again per cage. All of the excrement was collected per cage for the entire period in which weight records were kept. After weighing and homogenizing all of the excrement, a representative sample was taken from each cage for performing the analysis for zinc. The zinc excreted was calculated as a percentage of the zinc ingested.

Statistical Analysis:

An analysis of variance was carried out using the GLM procedure of the SAS statistical software.

Results

The results for the production parameters are shown in Table 3. Treatments T-1 to T-3 produced better production parameters relative to the control T-0, in all the periods. The consumption of feed was slightly less for the birds fed with zinc formate, which produced an improvement in the conversion index, but this was not significant. The administration of zinc in the form of zinc formate and methioninate (50 ppm) produced the same effect, treatment T-3 improved the production parameters significantly relative to treatments T-0, T-1 and T-2.

The results for zinc bioavailability are shown in Table 5. The highest bioavailability was observed in the treatments with zinc formate, zinc methioninate and the methioninate-formate complex, demonstrating greater absorption of this mineral form in the intestine.

Conclusions

The supplementation of diets for broilers with zinc in the form of salts of amino acid and formic acid at the doses laid down by the legislation produce an improvement in the production parameters. This improvement was more significant when the product administered was in the form of amino acid-zinc formate complex, owing to a synergistic effect of the two products combined. Moreover, said sources of zinc display greater bioavailability, so there is less emission of residues to the environment.

TABLE 11

Composition of the experimental diets %:

| | 0-21 d | 21-42 d |
|---|---|---|
| Ingredients | | |
| Wheat | 38.00 | 48.00 |
| Maize | 22.58 | 16.05 |
| Soya, 47% | 28.70 | 26.56 |
| Soya, extruded | 2.87 | 3.83 |
| Lard | 2.78 | 2.54 |
| DL-methionine | 0.259 | 0.238 |
| L-lysine HCl | 0.177 | 0.104 |
| Calcium carbonate | 1.269 | 0.697 |
| Dicalcium phosphate | 1.486 | 1.25 |
| Salt | 0.446 | 0.312 |
| Minerals and vitamins[1] | 0.400 | 0.400 |
| Choline chloride, 50% | 0.023 | 0.012 |
| Potato protein | 1.00 | |
| Analysis | | |
| Gross protein, % | 21.02 | 20.7 |
| Gross fat, % | 9.21 | 1.14 |
| Gross fiber, % | 4.85 | 1.02 |
| Moisture, % | 8.61 | 0.90 |

[1]Zinc-free vitamin-mineral supplement.

TABLE 12

Analysis of zinc content (ppm)

| Treatment | 0-21 d | 21-42 d |
|---|---|---|
| T-0 | 60.32 | 58.05 |
| T-1 | 61.35 | 59.75 |
| T-2 | 58.29 | 62.10 |
| T-3 | 62.35 | 60.25 |
| T-0 | 60.32 | 58.05 |
| T-1 | 61.35 | 59.75 |
| T-2 | 58.29 | 62.10 |
| T-3 | 62.35 | 60.25 |

TABLE 13

Production parameters

| | 0-21 days | | | | 21-42 days | | | | 0-42 days | | |
|---|---|---|---|---|---|---|---|---|---|---|---|
| Treatment | LW 21 d (g) | MDG (g) | MDC (g/d) | IC | LW 42 d (g) | MDG (g) | MDC (g/d) | IC | MDG (g) | MDC (g/d) | IC |
| T-0 | 705[a] | 33.6[a] | 47.3 | 1.40[a] | 2250[a] | 73.6[a] | 156.3 | 2.12[a] | 53.5[a] | 101.7 | 1.90[a] |
| T-1 | 740[b] | 35.2[b] | 48.3 | 1.37[b] | 2310[b] | 74.8[b] | 152.5 | 2.03[b] | 55.0[b] | 100.4 | 1.82[b] |
| T-2 | 750[b] | 35.7[b] | 48.1 | 1.35[b] | 2340[b] | 75.7[b] | 155.2 | 2.05[b] | 55.7[b] | 101.7 | 1.82[b] |
| T-3 | 790[c] | 37.6[c] | 50.5 | 1.34[c] | 2430[c] | 78.1[c] | 150.2 | 1.92[c] | 57.8[c] | 100.4 | 1.73[c] |
| Sig. | * | * | N.S | * | * | * | N.S | * | * | N.S | * |

[a], [b], [c]: Values in the same column with different superscript differ significantly (P < 0.05)
LW: Live weight; MDG: mean daily gain; MDC: mean daily consumption; IC: index of conversion Sig.: significance

TABLE 14

Zinc balance from 43 to 46 days of age:

| Treatment | Consumption of feed (g) | Zinc ingested (mg) | Zinc excreted (mg) | Bioavailability % |
|---|---|---|---|---|
| T-0 | 206 | 12.4$^a$ | 8.34$^a$ | 33.0$^a$ |
| T-1 | 222 | 13.3$^a$ | 7.20$^b$ | 45.8$^b$ |
| T-2 | 210 | 12.6$^a$ | 7.35$^b$ | 42.6$^b$ |
| T-3 | 206 | 12.4$^a$ | 6.01$^c$ | 51.5$^c$ |
| Sig. | N.S. | N.S. | * | * |

$^{a,b,c}$Values in the same column with different superscript differ significantly (P < 0.05)

Example 13

Test in Broilers

Objectives:

To compare the effectiveness of the copper aminoate (methioninate) products with copper formate and with the product obtained by combining both compounds which will be called copper methioninate-formate complex hereinafter, on the production parameters for broilers.

Material and Methods

Animals and Housing:

500 one-day old broilers of the Ross strain were used (without differentiation of sexes), housed in 20 pens of 4 m$^2$.

Experimental Treatments

Four experimental treatments were used, comprising the same basic diet supplemented with different sources of copper:

T-0: Base diet+25 ppm of copper in the form of copper sulfate

T-1: Base diet+25 ppm of copper in the form of copper formate

T-2: Base diet+25 ppm of copper in the form of copper methioninate

T-3: Base diet+25 ppm of copper in the form of copper methioninate-formate complex The dose of copper was calculated taking into account the copper content of the ingredients and the copper requirements in the case of treatments T-0 to T-3. The composition of the diets and their analysis are presented in Tables 1 and 2.

Controls

Control of production parameters was effected at 21 and 42 days of age, recording the live weight and the consumption of feed per batch.

On day 42 of the experiment, 2 animals were selected at random from each batch and were placed in cages in pairs according to their origin with respect to batch and previous treatment. During the next 4 days, an investigation of copper bioavailability was carried out. After fasting for 20 hours, the live weight per cage was recorded and the experimental feeds were supplied for 2 days, recording the consumption of feed. After fasting again for 20 hours, the birds were weighed again per cage. All of the excrement was collected per cage for the entire period in which weight records were kept. After weighing and homogenizing all of the excrement, a representative sample was taken from each cage for performing the analysis for copper. The copper excreted was calculated as a percentage of the copper ingested.

Statistical Analysis:

An analysis of variance was carried out using the GLM procedure of the SAS statistical software.

Results

The results for the production parameters are shown in Table 3. Treatments T-1 to T-3 produced better production parameters relative to the control T-0, in all the periods. The consumption of feed was slightly less for the birds fed with copper formate, which produced an improvement in the conversion index, but this was not significant. The administration of copper in the form of copper formate and methioninate (25 ppm) produced the same effect, treatment T-3 improved the production parameters significantly relative to treatments T-0, T-1 and T-2.

The results for copper bioavailability are shown in Table 5. The highest bioavailability was observed in the treatments with copper formate, copper methioninate and the methioninate-formate complex, demonstrating greater absorption of this mineral form in the intestine.

Conclusions

The supplementation of diets for broilers with copper in the form of salts of methionine and formic acid at the doses laid down by the legislation produce an improvement in the production parameters. This improvement was more significant when the product administered was in the form of copper methioninate-formate complex, owing to a synergistic effect of the two products combined. Moreover, said sources of copper display greater bioavailability, so there is less emission of residues to the environment.

TABLE 15

Composition of the experimental diets %:

| | 0-21 d | 21-42 d |
|---|---|---|
| Ingredients | | |
| Wheat | 38.00 | 48.00 |
| Maize | 22.58 | 16.05 |
| Soya, 47% | 28.70 | 26.56 |
| Soya, extruded | 2.87 | 3.83 |
| Lard | 2.78 | 2.54 |
| DL-methionine | 0.259 | 0.238 |
| L-lysine HCl | 0.177 | 0.104 |
| Calcium carbonate | 1.269 | 0.697 |
| Dicalcium phosphate | 1.486 | 1.25 |
| Salt | 0.446 | 0.312 |
| Minerals and vitamins[1] | 0.400 | 0.400 |
| Choline chloride, 50% | 0.023 | 0.012 |
| Potato protein | 1.00 | |
| Analysis | | |
| Gross protein, % | 21.02 | 20.7 |
| Gross fat, % | 9.21 | 1.14 |
| Gross fiber, % | 4.85 | 1.02 |
| Moisture, % | 8.61 | 0.90 |

[1]Copper-free vitamin-mineral supplement.

TABLE 16

Analysis of copper content (ppm)

| Treatment | 0-21 d | 21-42 d |
|---|---|---|
| T-0 | 31.5 | 32.8 |
| T-1 | 33.5 | 32.5 |
| T-2 | 32.7 | 33.0 |
| T-3 | 33.8 | 35.5 |

TABLE 17

Production parameters

| | 0-21 days | | | | 21-42 days | | | | 0-42 days | | |
|---|---|---|---|---|---|---|---|---|---|---|---|
| Treatment | LW 21 d (g) | MDG (g) | MDC (g/d) | IC | LW 42 d (g) | MDG (g) | MDC (g/d) | IC | MDG (g) | MDC (g/d) | IC |
| T-0 | 695 $^a$ | 31.6 $^a$ | 45.3 | 1.43 $^a$ | 2200 $^a$ | 71.6 $^a$ | 160.1 | 2.23 $^a$ | 51.6 $^a$ | 102.7 | 1.99 $^a$ |
| T-1 | 730 $^b$ | 34.2 $^b$ | 47.3 | 1.38 $^b$ | 2350 $^b$ | 77.1 $^c$ | 158.3 | 2.05 $^b$ | 55.2 $^b$ | 103.0 | 1.87 $^b$ |
| T-2 | 750 $^b$ | 34.7 $^b$ | 47.1 | 1.36 $^b$ | 2300 $^b$ | 73.8 $^b$ | 154.0 | 2.08 $^b$ | 54.0 $^b$ | 100.5 | 1.86 $^b$ |
| T-3 | 775 $^c$ | 39.6 $^c$ | 53.5 | 1.35 $^b$ | 2450 $^c$ | 79.7 $^c$ | 152.5 | 1.92 $^c$ | 57.6 $^c$ | 103.0 | 1.78 $^c$ |
| Sig. | * | * | N.S | * | * | * | N.S | * | * | N.S | * |

$^a, ^b, ^c$: Values in the same column with different superscript differ significantly (P < 0.05)
LW: Live weight; MDG: mean daily gain; MDC: mean daily consumption; IC: index of conversion Sig.: significance

TABLE 18

Copper balance from 43 to 46 days of age:

| Treatment | Consumption of feed (g) | Copper ingested (mg) | Copper excreted (mg) | Bioavailability % |
|---|---|---|---|---|
| T-0 | 206 | 67.98 $^a$ | 20.4 $^a$ | 30.0 $^a$ |
| T-1 | 222 | 73.26 $^a$ | 36.9 $^b$ | 50.5 $^b$ |
| T-2 | 210 | 69.3 $^a$ | 29.5 $^b$ | 42.6 $^b$ |
| T-3 | 206 | 68.0 $^a$ | 37.7 $^c$ | 55.5 $^c$ |
| Sig. | N.S. | N.S. | * | * |

$^a,^b,^c$Values in the same column with different superscript differ significantly (P < 0.05)

Example 14

Test of Efficacy in Piglets

Objectives:

To compare the effectiveness of the zinc aminoate (glycinate) and zinc formate products and the product obtained by combining both compounds which will be called zinc complex hereinafter, on the production parameters for recently weaned piglets.

Material and Methods

Animals and Housing:

48 piglets were used (Large White * Large White x Landrace), 50% males and 50% females, weaned at 21 days of age and housed in 8 pens with 6 animals in each (3 males and 3 females).

Experimental Treatments

Five experimental treatments were used, comprising the same basic diet, to which different sources of zinc were added:

T-0: Base diet+130 ppm of zinc in the form of zinc oxide

T-1: Base diet+130 ppm of zinc in the form of zinc formate

T-2: Base diet+130 ppm of zinc in the form of zinc glycinate

T-3: Base diet+130 ppm of zinc in the form of zinc glycinate-formate complex

The zinc dose was calculated taking into account the zinc content of the ingredients and the maximum permitted dose (150 ppm) in all the treatments.

The composition of the diets and their analysis are presented in Tables 1 and 2.

The experimental period was 29 days.

Controls

Control of production parameters was effected at the end of the experiment, recording the live weight, the daily growth and the consumption of feed.

At the end of the experiment, one male and one female were selected at random from each batch to take a specimen of liver tissue and determine the zinc content.

Statistical Analysis:

An analysis of variance was carried out using the GLM procedure of the SAS statistical software.

Results

The results for the production parameters are shown in Table 3. Treatments T-1 to T-3 produced better production parameters relative to the control, in all the periods. The consumption of feed was slightly less for the piglets fed with the organic sources of zinc, which produced an improvement in the conversion index.

Conclusions

When the diet of piglets is supplemented with zinc in the form of salts of formic and amino acid at the doses laid down by the legislation, there is an improvement in the production parameters, which can be regarded as a growth-promoter effect. The improvements were greater when the zinc was administered in the form of zinc glycinate-formate complex. Moreover, these sources of zinc display greater bioavailability, so that there is less emission of residues to the environment.

TABLE 19

Composition of the experimental diets:

| Ingredients | |
|---|---|
| Maize | 30.0 |
| Wheat | 5.0 |
| Barley | 15.0 |
| Soya (full fat) | 14.0 |
| Fish meal | 9.9 |
| Soya flour (47%) | 2.0 |
| Soya oil | 1.9 |
| Delactosed whey | 3.1 |
| Sweet whey | 17.0 |
| L-lysine (78%) | 0.2 |
| L-threonine (99%) | 0.14 |
| Methionine-OH | 0.18 |
| Calcium carbonate | 0.34 |

TABLE 19-continued

Composition of the experimental diets:

| Dicalcium phosphate | 0.85 |
|---|---|
| Vitamin-mineral complex[1] | 0.3 |
| Analysis | |
| Gross protein, % | 21.02 |
| Gross fat, % | 7.20 |
| Gross fiber, % | 2.52 |
| Moisture, % | 8.40 |

[1]Zinc-free vitamin-mineral supplement.

TABLE 20

Analysis of zinc content in the diets (ppm)

| Treatment | Zinc |
|---|---|
| T-0 | 153.4 |
| T-1 | 133.5 |
| T-2 | 155.4 |
| T-3 | 145.3 |

TABLE 21

Production parameters from 21 to 50 days:

| | 21-50 days | | | |
|---|---|---|---|---|
| Treatment | GLW 21-50 d (kg) | MDG (g) | MDC (g/d) | IC |
| T-0 | 11.40 [a] | 393.1 [a] | 795.3 | 2.02 [a] |
| T-1 | 12.50 [b] | 431.0 [b] | 752.3 | 1.75 [b] |
| T-2 | 12.75 [b] | 439.6 [b] | 741.3 | 1.68 [b] |
| T-3 | 13.70 [c] | 472.4 [c] | 763.2 | 1.62 [c] |
| Sig. | * | * | N.S | * |

[a], [b], [c]: Values in the same column with different superscript differ significantly (P < 0.05)
LW: Live weight; MDG: mean daily gain; MDC: mean daily consumption; IC: index of conversion; GLW: gain in live weight
S.E: Standard error; Sig.: significance Example 15

Test of Efficacy in Piglets

Objectives:

To compare the effectiveness of the copper glycinate (glycinate) and copper formate products and the product obtained by combining both compounds which will be called copper complex hereinafter, on the production parameters for recently weaned piglets.

Material and Methods

Animals and Housing:

48 piglets were used (Large White * Large White x Landrace), 50% males and 50% females, weaned at 21 days of age and housed in 8 pens with 6 animals in each (3 males and 3 females).

Experimental Treatments

Five experimental treatments were used, comprising the same basic diet, to which different sources of copper were added:

T-0: Base diet+125 ppm of copper in the form of copper sulfate

T-1: Base diet+125 ppm of copper in the form of copper formate

T-2: Base diet+125 ppm of copper in the form of copper glycinate

T-3: Base diet+125 ppm of copper in the form of copper glycinate-formate complex The copper dose was calculated taking into account the copper content of the ingredients and the maximum permitted dose (175 ppm) in all the treatments.

The composition of the diets and their analysis are presented in Tables 1 and 2.

The experimental period was 21 days.

Controls

Control of production parameters was effected at the end of the experiment, recording the live weight, the daily growth and the consumption of feed.

At the end of the experiment, one male and one female were selected at random from each batch to take a specimen of liver tissue and determine the copper content.

Statistical Analysis:

An analysis of variance was carried out using the GLM procedure of the SAS statistical software.

Results

The results for the production parameters are shown in Table 3. Treatments T-1 to T-3 produced better production parameters relative to the control, in all the periods. The consumption of feed was slightly less for the piglets fed with the organic sources of copper, which produced an improvement in the conversion index.

Conclusions

When the diet of piglets is supplemented with copper in the form of salts of formic and amino acid at the doses laid down by the legislation, there is an improvement in the production parameters, which can be regarded as a growth-promoter effect. The improvements were greater when the copper was administered in the form of copper glycinate-formate complex. Moreover, these sources of copper display greater bioavailability, so that there is less emission of residues to the environment.

TABLE 22

Composition of the experimental diets:

| Ingredients | |
|---|---|
| Maize | 30.0 |
| Wheat | 5.0 |
| Barley | 15.0 |
| Soya (full fat) | 14.0 |
| Fish meal | 9.9 |
| Soya flour (47%) | 2.0 |
| Soya oil | 1.9 |
| Delactosed whey | 3.1 |
| Sweet whey | 17.0 |
| L-lysine (78%) | 0.2 |
| L-threonine (99%) | 0.14 |
| Methionine-OH | 0.18 |
| Calcium carbonate | 0.34 |

TABLE 22-continued

Composition of the experimental diets:

| | |
|---|---|
| Dicalcium phosphate | 0.85 |
| Vitamin-mineral complex[1] | 0.3 |
| Analysis | |
| Gross protein, % | 21.02 |
| Gross fat, % | 7.20 |
| Gross fiber, % | 2.52 |
| Moisture, % | 8.40 |

[1] Copper-free vitamin-mineral supplement.

TABLE 23

Analysis of copper content in the diets (ppm)

| Treatment | Copper |
|---|---|
| T-0 | 140.5 |
| T-1 | 143.5 |
| T-2 | 138.5 |
| T-3 | 140.0 |

TABLE 24

Production parameters from 21 to 42 days:

| | 21-42 days | | | |
|---|---|---|---|---|
| Treatment | GLW 21-42 d (kg) | MDG (g) | MDC (g/d) | IC |
| T-0 | 6.5 $^a$ | 309.5 $^a$ | 650.5 | 2.10 $^a$ |
| T-1 | 7.5 $^b$ | 360.5 $^b$ | 665.0 | 1.85 $^b$ |
| T-2 | 7.25$^b$ | 345.0 $^b$ | 660.5 | 1.91 $^b$ |
| T-3 | 7.75$^c$ | 370.0 $^c$ | 650.5 | 1.75 $^c$ |
| Sig. | * | * | N.S | * |

$^a, ^b, ^c$: Values in the same column with different superscript differ significantly (P < 0.05)
LW: Live weight; MDG: mean daily gain; MDC: mean daily consumption; IC: index of conversion; GLW: gain in live weight
S.E: Standard error; Sig.: significance

Example 16

Test in Broilers

Objectives:

To compare the effectiveness of the zinc carboxylate (zinc formate) products and the product obtained by combining the zinc salt of the hydroxy analog of methionine and zinc carboxylate.

Material and Methods

Animals and Housing:

160 one-day old broilers of the Ross strain were used (without differentiation of sexes), housed in cages in groups of 10 animals.

Experimental Treatments

Two experimental treatments were used, comprising the same basic diet to which different sources of zinc were added:

T-1: Base diet+150 ppm of zinc in the form of zinc formate

T-2: Base diet+150 ppm of zinc in the form of methionine hydroxy analog-zinc formate complex Controls Control of production parameters was effected at 21 days of age, recording the live weight and the consumption of feed per batch.

Statistical Analysis:

An analysis of variance was carried out using the GLM procedure of the SAS statistical software.

Results

The results for the production parameters are shown in Table 3. Treatment T-2 produced better production parameters relative to the control T-1, in this period. The consumption of feed was slightly less for the birds fed with zinc formate-methioninate hydroxy analog complex, which produced an improvement in the conversion index.

Conclusions

The supplementation of diets for broilers with zinc in the form of formate-methionine hydroxy analog complexes at the doses laid down by the legislation produce an improvement in the production parameters.

TABLE 25

Composition of the experimental diets %:

| | 0-21 d |
|---|---|
| Ingredients | |
| Wheat | 38.00 |
| Maize | 22.58 |
| Soya, 47% | 28.70 |
| Soya, extruded | 2.87 |
| Lard | 2.78 |
| DL-methionine | 0.259 |
| L-lysine HCl | 0.177 |
| Calcium carbonate | 1.269 |
| Dicalcium phosphate | 1.486 |
| Salt | 0.446 |
| Minerals and vitamins[1] | 0.400 |
| Choline chloride, 50% | 0.023 |
| Potato protein | 1.00 |
| Analysis | |
| Gross protein, % | 21.02 |
| Gross fat, % | 9.21 |
| Gross fiber, % | 4.85 |
| Moisture, % | 8.61 |

[1] Zinc-free vitamin-mineral supplement.

TABLE 26

Analysis of zinc content (ppm)

| Treatment | 0-21 d |
|---|---|
| T-1 | 160 |
| T-2 | 165 |

TABLE 27

Production parameters 0-21 days

| Treatment | LW 21 d (g) | MDG (g) | MDC (g/d) | IC |
|---|---|---|---|---|
| T-1 | 790 [b] | 37.6 [b] | 47.5 | 1.26 [b] |
| T-2 | 820 [a] | 39.0 [a] | 47.0 | 1.20 [a] |
| Sig. | * | * | N.S | * |

[a, b]: Values in the same column with different superscript differ significantly ($P < 0.05$)
LW: Live weight; MDG: mean daily gain; MDC: mean daily consumption; IC: index of conversion
Sig.: significance

Example 17

Test of Efficacy in Piglets

Objectives:

To compare the effectiveness of the zinc carboxylate (zinc formate) products and the product obtained by combining the zinc salt of the hydroxy analog of methionine and the zinc carboxylate in recently weaned piglets.

Material and Methods

Animals and Housing:

24 piglets were used (Large White * Large White x Landrace), 50% males and 50% females, weaned at 21 days of age and housed in 4 pens with 6 animals in each (3 males and 3 females).

Experimental Treatments

Two experimental treatments were used, comprising the same basic diet, to which different sources of zinc were added:

T-1: Base diet+150 ppm of zinc in the form of zinc formate
T-2: Base diet+150 ppm of zinc in the form of methionine hydroxy analog-zinc formate complex The zinc dose was calculated taking into account the zinc content of the ingredients and the maximum permitted dose (150 ppm) in all the treatments.

The composition of the diets and their analysis are presented in Tables 1 and 2.

The experimental period was 20 days.

Controls

Control of production parameters was effected at the end of the experiment, recording the live weight, the daily growth and the consumption of feed.

Statistical Analysis:

An analysis of variance was carried out using the GLM procedure of the SAS statistical software.

Results

The results for the production parameters are shown in Table 3. Treatment T-2 produced better results with respect to conversion index and growth than treatment T-1. These data corroborate the previous experiments conducted on fattening chicken.

Conclusions

When the diet of piglets is supplemented with zinc in the form of salts of methionine hydroxy analog-zinc formate complexes at the doses laid down by the legislation, there is an improvement in the production parameters, which can be regarded as a growth-promoter effect.

TABLE 28

Composition of the experimental diets:

| Ingredients | |
|---|---|
| Maize | 28.0 |
| Barley | 17.0 |
| Soya (full fat) | 15.0 |
| Fish meal | 10.0 |
| Soya flour (47%) | 2.0 |
| Soya oil | 2.0 |
| Delactosed whey | 2.0 |
| Sweet whey | 19.0 |
| L-lysine (78%) | 0.2 |
| L-threonine (99%) | 0.14 |
| Methionine-OH | 0.15 |
| Calcium carbonate | 0.35 |
| Dicalcium phosphate | 0.85 |
| Vitamin-mineral complex[1] | 0.3 |
| Analysis | |
| Gross protein, % | 21.0 |
| Gross fat, % | 7.5 |
| Gross fiber, % | 3.0 |
| Moisture, % | 7.5 |

[1] Zinc-free vitamin-mineral supplement.

TABLE 29

Analysis of zinc content in the diets (ppm)

| Treatment | Zinc |
|---|---|
| T-1 | 165.4 |
| T-2 | 168.5 |

TABLE 30

Production parameters from 21 to 41 days:

21-41 days

| Treatment | GLW 21-41 d (kg) | MDG (g) | MDC (g/d) | IC |
|---|---|---|---|---|
| T-1 | 8.00 [b] | 400.0 [b] | 655.0 | 1.63 [b] |
| T-2 | 9.00 [b] | 450.0 [a] | 660.0 | 1.47 [a] |
| Sig. | N.S. | * | N.S | * |

[a, b, c]: Values in the same column with different superscript differ significantly ($P < 0.05$)
LW: Live weight; MDG: mean daily gain; MDC: mean daily consumption; IC: index of conversion; GLW: gain in live weight
S.E: Standard error; Sig.: significance

The invention claimed is:

1. A process for preparing a feed supplement that promotes growth in animals comprising the steps of:
   (i) preparing a dry metal carboxylate of formula $M(RCOOH)_2$, wherein M is a $Zn^{2+}$ or $Cu^{2+}$ cation of a divalent metal and R is H or a $CH_3(CH_2)_2$ group, by (a) mixing a carboxylic acid with a basic salt of the divalent metal to form a first reaction mixture that undergoes an exothermic reaction to form the metal carboxylate and water, and (b) stirring to remove water;
   (ii) preparing a metal aminoate by (a) mixing water, a compound comprising the divalent metal, and an amino acid selected from the group consisting of glycine and methionine to form a second reaction mixture, (b) stirring the second reaction mixture to promote an exothermic reaction that forms the metal aminoate and water, and (c) removing water from the second reaction mixture; and (iii) mixing the dry metal carboxylate and the metal aminoate under conditions that form a complex comprising the metal carboxylate and the metal aminoate and water, and removing the water to form a dry metal complex of the metal carboxylate and the metal aminoate, wherein, when administered to an animal in its feed, a bioavailability of the divalent metal in the dry metal complex is different than the bioavailability of the divalent metal in either the dry metal carboxylate or the metal aminoate alone.

2. The process according to claim 1, wherein the basic salt, in step (i) is zinc oxide or copper oxide.

3. The process according to claim 1, wherein the divalent metal compound in step (ii) is zinc sulphate or copper sulphate.

4. The process according to claim 1, wherein the dry metal complex comprises carboxylate and aminoate in a weight ratio of 30/70 to 70/30.

5. The process according to claim 1, wherein water is removed in steps (ii) and (iii) by vacuum and with intensifier turbines operating between 1500-3000 rpm.

6. The process according to claim 5, wherein the removal of water in step (iii) is carried out at a temperature between 80° C. and 100° C.

7. The process according to claim 5, wherein the removal of water is carried out with an absorbent.

8. The process according to claim 5, further comprising grinding the dry metal complex.

9. A process for preparing a compound that promotes growth in animals comprising the steps of:

(i) mixing a carboxylic acid selected from the group consisting of formic acid and butyric acid with a hydroxy analog of methionine to form a first mixture;

(ii) mixing the first mixture with a basic compound of a divalent metal comprising $Zn^{2+}$ or $Cu^{2+}$ to form a reaction mixture that undergoes an exothermic reaction to form a complex comprising a carboxylate- methioninate hydroxy analog of the divalent metal and water, and (iii) removing water to recover a dry metal complex of the carboxylate and methioninate hydroxy analog, wherein, when administered to an animal in its feed, a bioavailability of the divalent metal in the dry metal complex is different than the bioavailability of the divalent metal in either the dry metal carboxylate or the metal aminoate alone.

10. The process according to claim 9, wherein the carboxylic acid, the hydroxy analog of methionine and the basic compound are mixed in step (ii) in a molar proportion of 2:2:2.

11. The process according to claim 9, wherein the mixing in step (i) is carried out in a first reactor and the mixing in step (ii) is carried out in a second reactor.

12. The process according to claim 11, wherein the mixing in step (ii) is carried out by providing the second reactor with the basic compound and then adding the first mixture to the second reactor.

13. The process according to claim 9, wherein the mixing in step (ii) is carried out at a speed of 200-600 rpm.

14. The process according to claim 9, wherein the water is removed under vacuum with stirring with a delumping intensifier turbine at a speed of 1500-3000 rpm.

15. The process according to claim 14, wherein the removal of water is carried out with heating at a temperature between 80° C. and 130° C.

16. An animal feed supplement comprising a complex of a divalent metal carboxylate and an aminoate or hydroxyl analog thereof, wherein the bioavailability of the divalent metal in the complex is better than the bioavailability of the divalent metal in the carboxylate alone.

17. The animal feed supplement according to claim 16, wherein the complex is formed from a dry metal carboxylate of formula $M(RCOOH)_2$, wherein M is a $Zn^{2+}$ or $Cu^{2+}$ cation of a divalent metal and R is H or a $CH_3(CH_2)_2$ group, and an aminoate comprising glycine or methionine and the cation.

18. The animal feed supplement according to claim 17, wherein the complex comprises carboxylate and aminoate in a weight ratio of 30/70 to 70/30.

19. The animal feed supplement according to claim 17, wherein the complex comprises zinc formate and glycinate.

20. The animal feed supplement according to claim 17, wherein the complex comprises zinc formate and the hydroxy analog of methionine.

21. The animal feed supplement according to claim 17, wherein the complex comprises copper formate and the hydroxy analog of methionine.

22. The animal feed supplement according to claim 16, wherein the complex comprises a dry metal carboxylate of formula $M(RCOOH)_2$, wherein M is a $Zn^{2+}$ or $Cu^{2+}$ cation of a divalent metal and R is H or a $CH_3(CH_2)_2$ group, and a hydroxy analog of methionine.

23. The animal fee supplement according to claim 22, wherein the complex comprises zinc formate and the hydroxy analog of methionine.

* * * * *